(12) United States Patent
Petrov et al.

(10) Patent No.: US 6,469,137 B1
(45) Date of Patent: Oct. 22, 2002

(54) MYELOPEPTIDES AND THEIR THERAPEUTIC USE

(75) Inventors: Rem V. Petrov, Moscow (RU); Augusta A. Mikhailova, Moscow (RU); Larissa A. Fonina, Moscow (RU); Sergei A. Guriyanov, Moscow (RU)

(73) Assignee: Primamedic, Ltd (CY)

( * ) Notice: Subject to any disclaimer, the term of this patent is extended or adjusted under 35 U.S.C. 154(b) by 0 days.

(21) Appl. No.: 09/341,173

(22) PCT Filed: Jan. 7, 1998

(86) PCT No.: PCT/GB98/00030

§ 371 (c)(1), (2), (4) Date: Sep. 7, 1999

(87) PCT Pub. No.: WO98/30581

PCT Pub. Date: Jul. 16, 1998

(30) Foreign Application Priority Data

Jan. 7, 1997 (GB) ................................................ 9700154

(51) Int. Cl.$^7$ .................................................. C07K 7/06
(52) U.S. Cl. ........................ 530/329; 530/328; 530/330; 514/16; 514/17
(58) Field of Search ................................ 530/329, 330, 530/328; 514/17, 16

(56) References Cited

FOREIGN PATENT DOCUMENTS

| WO | 9501182 | 1/1995 |
| WO | 9530007 | 11/1995 |
| WO | 9610634 | 4/1996 |
| WO | 9618652 | 6/1996 |
| WO | 97/43417 | * 11/1997 |

OTHER PUBLICATIONS

Tuazon, Biochemistry 36, 16059, 1997.*
Petrov, Rem V. et al. (1997) "Bone marrow immunoregulatory peptides (myelopeptides): isolation, structure, and functional activity" *Biopolymers* 43(2):139–146.
Poloni, Francesca et al. (1995) "Selection of phage–displayed peptides mimicking an extracellular epitope of human MDR1–P–glycoprotein" *Physiol. Chem. Phys. Med. NMR* 27:271–280.
Herman, Z.S. et al. (1980) "Analgesic Activity of Some Tuftsin Analogs" 67(12):613–614.

* cited by examiner

*Primary Examiner*—Christopher S. F. Low
*Assistant Examiner*—David Lukton
(74) *Attorney, Agent, or Firm*—Saliwanchik, Lloyd & Saliwanchik

(57) ABSTRACT

The present invention pertains to peptides comprising 4 to 10 amino acids including $X^1$-Pro, Pro-$X^2$ or $X^1$-Pro-$X^2$, wherein $X^1$ and $X^2$ are independently selected from Lys, Arg, His, Asp, Glu, Asn and Gin, and the other amino acids are independently selected from Gly, Ala, Val, Leu, Ile, Nle, Nva, Pro, Phe, Tyr, Trp, Cys, Met, Ser and Thr. Such peptides, including LVCYPQ (SEQ ID NO: 3), FRPRIMTP (SEQ ID NO: 4), VVYPD (SEQ ID NO: 5) and VDPP (SEQ ID NO: 6), are obtainable from porcine bone marrow cell culture, and have immunostimulating and anti-viral properties.

16 Claims, No Drawings

SEQUENCE LISTING

```
<160> NUMBER OF SEQ ID NOS: 6

<210> SEQ ID NO 1
<211> LENGTH: 6
<212> TYPE: PRT
<213> ORGANISM: Sus species

<400> SEQUENCE: 1

Phe Leu Gly Phe Pro Thr
 1               5

<210> SEQ ID NO 2
<211> LENGTH: 6
<212> TYPE: PRT
<213> ORGANISM: Sus species

<400> SEQUENCE: 2

Leu Val Val Tyr Pro Trp
 1               5

<210> SEQ ID NO 3
<211> LENGTH: 6
<212> TYPE: PRT
<213> ORGANISM: Sus species

<400> SEQUENCE: 3

Leu Val Cys Tyr Pro Gln
```

-continued

```
<210> SEQ ID NO 4
<211> LENGTH: 8
<212> TYPE: PRT
<213> ORGANISM: Sus species

<400> SEQUENCE: 4

Phe Arg Pro Arg Ile Met Thr Pro
 1               5

<210> SEQ ID NO 5
<211> LENGTH: 5
<212> TYPE: PRT
<213> ORGANISM: Sus species

<400> SEQUENCE: 5

Val Val Tyr Pro Asp
 1               5

<210> SEQ ID NO 6
<211> LENGTH: 4
<212> TYPE: PRT
<213> ORGANISM: Sus species

<400> SEQUENCE: 6

Val Asp Pro Pro
 1
```

MYELOPEPTIDES AND THEIR THERAPEUTIC USE

FIELD OF THE INVENTION

This invention relates to myelopeptides and their therapeutic use.

BACKGROUND OF THE INVENTION

As reported by Mikhailova et al, Immun. Lett. 47:199–203 (1995), and in WO-A-9618652, the bone marrow cells of various animals and humans produce a group of bioregulatory peptides named myelopeptides (MPs). MPs have a wide spectrum of functional activities: immunoregulatory, differentiating and opiate-like. They evoke 2–3-fold stimulation of antibody production to various antigens and correct some immune disorders. MPs influence the differentiation of bone marrow and peripheral blood cells derived from healthy and leukemic donors. They induce terminal differentiation in the leukemic human HL-60 cell line, and show an effect on pain sensitivity.

More specifically, Mikhailova et al report two specific hexapeptides having immunoregulatory properties, i.e. FLGFPT (designated hereinafter as MP-1) (SEQ ID NO: 1) and LVVYPW (designated hereinafter as MP-2) (SEQ ID NO: 2). WO-A-9618652 discloses hexapeptides, having antitumour activity, of the formula $Y^1$-$Y^2$-$Y^3$-Tyr-P-Trp. An example is MP-2.

SUMMARY OF THE INVENTION

Further peptides have been isolated from the supernatant of porcine bone marrow cell culture by means of successive solid phase extraction and HPLC. These novel peptides are of the type comprising 4 to 10 amino-acids including Pro-X and/or X-Pro, X being a hydrophilic amino-acid, and which typically otherwise comprise hydrophobic amino-acids.

The novel peptides have therapeutic utility. For example, they may be used where immunostimulating or antiviral activity is required. In particular, they may induce production of interferon(s), inhibit replication of viruses, including HIV, thereby providing a protective effect in mammals, and increase immune resistance towards bacterial infection.

DESCRIPTION OF THE INVENTION

As indicated above, certain novel peptides have been obtained from natural sources, using conventional procedures. They or other peptides of the invention may also be prepared by synthetic procedures that are known to those of ordinary skill in the art, e.g. the well known solid phase method.

Various preferred characteristics of the novel peptides are defined in the claims. They may be tetra-, penta-, hexa-, hepta-, octa-, nona- or deca-peptides. Specific examples are LVCYPQ (designated hereinafter as MP-3) (SEQ ID NO: 3), FRPRIMTP (designated hereinafter as MP-4) (SEQ ID NO: 4), VVYPD (designated hereinafter as MP-5) (SEQ ID NO: 5) and VDPP (designated hereinafter as MP-6) (SEQ ID NO: 6), and data for these peptides are presented below. As will be evident from the results, these peptides do not have uniform characteristics. It will however also be evident that suitable tests can be made, to determine which is most suited for any particular application.

Peptides of the invention may be made up into pharmaceutical formulations of any suitable type, using known carriers or diluents, e.g. as solutions or dispersions to be administered, with or without an adjuvant. The amount of the peptide that is administered will be chosen with regard to factors such as the route of administration, the severity of the conditions, the age and health of the patient etc. The skilled physician will be able to select appropriate amounts, e.g. based on the effective dosages reported in the following results. MP-3 Stimulates Macrophage Phagocytosis Phagocytosis of opsonized sheep red blood cells (SRBC) by murine peritoneal macrophages was measured in the NBT-test (reduction of nitro blue tetrazolium by superoxide anions released by macrophages during an oxidative burst). Peritoneal cells were obtained from mice (CBA×C57B1)F1 plated per well in 96-well flat-bottom plates ($1 \times 10^6$ cells/well) in 199 medium. After 2 h incubation at 37° C. in an atmosphere of 5% $CO_2$ in air, non-adherent cells were removed by vigorous washing with warmed Hank's balanced salt solution (BSS). 100 μl of NBT solution (1 mg/ml), 50 μl 1% suspension of opsonized SRBC and MP-3, MP-1 or MP-2 at concentrations from $10^{-6}$ to $10^{-18}$ g/ml were added to the wells. Control wells had no MPs. After 1 hour incubation at 37° C., the cells were washed with BSS and fixed with 10% formalin solution. 10 min later, the cells were washed with distilled water and dried. The insoluble blue formazan was solubilized by adding first 60 μl/well 2M KOH and then 70 μl/well dimethyl sulphoxide (DMSO). The contents of the wells were then mixed to complete solubilisation. The final solution had an intense turquoise-blue colour. The $OD_{620}$ was read on an ELISA reader Multiskan MCC/340. The level of phagocytosis in each well treated with MPs was compared to that in a control well (100%).

By contrast to MP-1 and MP-2, MP-3 stimulates macrophage phagocytosis in a dose-dependent manner. The dose curve has a bimodal character. Maximal stimulation, up to 250%, occurs at doses of $10^{-8}$–$10^{-7}$ g/ml. There is one more peak of macrophage stimulation (at doses of $10^{-16}$–$10^{-17}$ g/ml). This effect is less pronounced but statistically significant ($p<0.05$).

It may be concluded that the stimulation of macrophage phagocytosis by MP-3 results in its protective effect in infected animals.

MP-3 Increases the Survival of Mice Infected with *Salmonella typhimurium*

MP-3 was used to inoculate (CBA×C57BL)F1 mice 1/p at doses of $0.5 \times 10^{-4}$ g/mouse and $1 \times 10^{-6}$ g/mouse. 24 hours later, these mice were infected with various doses of *Salmonella typhimurium* 415 ($10^2$, $10^3$, $10^4$ or $10^5$ bacterial cells/mouse). The mice of a control group were inoculated with saline solution. Each group contained 10 mice. The life span of each mouse was followed over 21 days.

A pronounced protective effect of MP-3 was obtained at both doses used. At the level of 100% death in controls ($10^5$ and $10^4$ bacterial cells/mouse), survival in the groups treated with MP-3 was 70–90%. At the level of 50% death in a control ($10^2$ bacterial cells/mouse), all mice treated with MP-3 stayed alive. This suggests that MP-3 protects the animals from bacterial infection due to its ability to stimulate macrophage phagocytosis.

MPs Induce Resistance to Lethal Bacterial Infection Acute bacterial infection was induced in laboratory mice of (CBA×C57B1)F1 origin using an intraperitoneal injection of 100 $LD_{50}$ *Salmonella thyphi* which actually was 1,000 microbe bodies. The infection caused a rapidly progressing sepsis and death of 100% animals within 3 days of such challenge.

Placebo control animals were injected intraperitoneally or subcutaneously using 0.2 ml of 0.85% NaCl saline 24 h before challenge. Then these animals were subjected to the same procedure of infection using 100 $LD_{50}$ of *S. thyphi*. All the control animals died within 3 days, as if they were just challenged without any pre-treatment. By contrast, the pre-treatment of mice using intraperitoneal or subcutaneous injection of MP-3, MP-4, MP-5 or MP-6, 24 h before the lethal challenge by 100 $LD_{50}$ *S. thyphi*, saved most of the animals. The MP's protection was dose-dependent.

The MPs, used at 1–10 µg doses per mouse, defended 90–100% of animals from subsequent challenge by the lethal dose of Salmonella. Both routes of injection, intraperitoneal and subcutaneous, were shown to be quite effective for pre-treatment using the MPs.

MP-4 Induces Terminal Differentiation in Leukaemia Cells

HL-60 cell line was obtained from bone marrow cells of patients with acute myeloid leukemia. These cells are myelomonoblasts which are intensively proliferating. They can differentiate to granuloid or monocyte pathway only in the presence of appropriate stimulants.

The human myeloid HL-60 line was maintained in standard medium: RPMI-1640 medium supplemented with 15% (v/v) heat-inactivated fetal calf serum, 20 mM HEPES, 2 mM L-glutamine and 50 µg/ml gentamycin. The initial cell concentration was $2\times10^5$ cells/ml. The cells were cultivated at 37° C. in an atmosphere of 5% $CO_2$ in air. MP-4 was added to the culture at concentrations from $1\times10^{-2}$ to $1\times10^2$ g/ml. After 3 days of cultivation, the cells were washed and reincubated in fresh cultural medium. 3 days later, each culture was labelled with $^3H$-thymidine and $^{14}C$-glycine, 4 hours before termination of culture. The cells were harvested on the 6th day of cultivation and their DNA ($^3H$) and protein ($^{14}C$) radioactivity was measured. The mean counts per min (cpm) in triplicate culture were analyzed.

It is known that a decrease in chromosomal DNA synthesis and an increase of total protein synthesis without histones are characteristic of the differentiation process. From changes of the ratio of $^3H/^{14}C$ incorporation, it could be seen that MP-4 induces the differentiation process in HL-60 cells. The MP-4 effect on blastoid cells HL-60 is dose-dependent. The optimal dose is 0.1–5.0 µg/ml.

Morphological analysis of HL-60 cells treated with MP-4 confirmed these results. There were about 60% mature forms (monocytes-macrophages) among blastoid cells. The differentiating effect of MP-4 was compared with that of the known differentiating factors phorbol myristate acetate and maturation inducer (T-lymphocyte differentiating factor). It may be concluded that MP-4 induces terminal differentiation in leukemia HL-60 cells in the monocyte pathway.

Serum Interferon Increase Induced by MPs in Mice

Non-inbred white males mice aged 1.5–2 months, body weight 18–20 g, were injected in the peritoneal cavity, with a single dose of MP-3, MP-4, MP-5 or MP-6: 0.01, 0.1, 1 or 10 µg (per mouse). Each of the experimental groups of animals was represented by 25 mice receiving the same dose of a preparation. 4, 24, 48, 72 or 96 h after injection, 5 mice of each experimental group were sacrificed, their serum samples pooled and stored frozen at −60° C. until the interferon activity of the pooled serum measured. The latter measurement was performed by testing serum anti-viral activity in the in vitro cell cultures infected by encephalomyocarditis virus (EMV).

In more detail, cell cultures of L929 fibroblastoid cell line were grown in alpha-MEM culture medium supplemented with 10% FBS. Cultures of 200,000 cells suspended in 0.1 ml of the culture medium were placed into wells of 96-well microplate and incubated in an atmosphere of 5% $CO_2$ at 37° C. The L929 cell cultures were infected using 100 $TCIC_{50}$ dose of the established laboratory strain of EMV. Cytopathological damage in cell morphology was recorded 24 h from infection.

Factor 2 serial dilutions of each serum sample were made using alpha-MEM culture medium containing FBS. 0.1 ml of the designated dilution of serum sample was added into each microwell containing L929 cell culture at the point of its infection with EMV.

On observing L929 cell damage caused by EMV within 24 h, the highest dilution of a serum conferring 50% inhibition of the viral infection was recorded. The reverse value of such highest dilution was taken as an interferon titer of the serum represented in Units/ml.

In the control groups of mice, the strongest of known interferon inducers were used. Namely, Newcastle disease virus (NDS) and Ridostin were used as a positive control to be compared with MPs by their serum interferon-increasing activity.

Two phases of visible increase of early (4 h) and late (48 h) interferon were observed in the mouse serum after a single injection of Serum interferon levels of 40 and 80 units/ml were reached, at 0.1 µg MP-4.

A single injection of 0.01 µg MP-5 led to a very strong increase of late (48 h) serum interferon. The serum interferon titers reached 320 units/ml, the level characteristic Ridostin, one of the strongest interferon inducers yet known.

MP-3 and MP-6 weakly induced late interferon in the mouse serum. Levels of 20 and 40 units/ml, respectively, were achieved 48 h after a single injection of 1–10 µg MP-3 and 0.1–1 µg MP-6.

Anti-viral Activity of the MPs In Vitro

Being capable of inducing serum interferon increase in vivo, the MPs most probably induce synthesis of interferon in the appropriate cell culture in vitro. If so, this can be monitored according to these compounds' anti-viral action in cell culture in vitro, when infected by actively replicating virus.

In vitro culture of L929 mouse cells acutely infected by encephalomyocarditis virus (EMV) was used as a model to define active concentrations of MP-3, MP-4, MP-5 and MP-6 as related to their capability to induce interferon synthesis in mammalian cells and hence block viral infection in these cells. The L929 mouse fibroblastoid cell line was maintained in vitro as described above. MP-3, MP-4, MP-5 and MP-6 were added into triplicate cultures using the following final concentrations: 500, 250, 125, 63, 31, 16, 8, 4, 2, 1, 0.5, 0.25 µg per 1 ml of culture. Ridostin was used as a control interferon-inducer.

24 or 48 h post-injection, the L929 cell cultures were infected by 100 $TCID_{50}$ of EMV. During the next 24 h the viral infection caused dramatic damages in L929 cells. When the cultures were pre-incubated in the presence of MP-3, it did not prevent the cell layers from extensive damage caused by subsequent virus infection using 100 $TCID_{50}$ of EMV. MP-5, by contrast, when added in a final concentration of 16 µg/ml or more, completely abrogated destructive influence of the virus on L929 cells. So did MP-6, when added at a concentration of 4 µg/ml or more. The anti-viral effect of MP-5 and MP-6 was quite comparable to that of Ridostin added at 0.5 µg/ml or more. MP-4 also defended the L929 cells from the virus-induced damage, after 48 h exposure of the cells in the presence of 32 µg/ml (or higher concentration) of the preparation before their challenge by the virus.

Interferon Induction by MPs in Human Cells In Vitro

The interferon-inducing capacities of the MPs was examined in both L-41 human cell line and healthy donor peripheral blood cell (PBC) cultures. L-41 cells were maintained in medium 199 supplemented by 10% FBS and antibiotics. 200,000 cells per 1 ml of culture medium were placed in the wells of 24-well plastic culture plates and grown at 37° C. in the atmosphere of 5% $CO_2$. When a cell monolayer was formed, the control and experimental interferon-inducers were introduced in the cultures in the centration desired. 24 h after interferon induction, the culture supernatants were harvested and then examined for interferon content.

The healthy donor PBC were incubated in the wells of 96-well culture plates and the culture supernatants were harvested 24 h after the test preparation was added to the culture.

To measure the interferon activity of the supernatants harvested, serial dilutions of the supernatants were prepared and then added into fresh L-41 cultures infected using 100 $TCID_{50}$ of EMV. The interferon titer of the supernatant was recorded, as described above for interferon titration of the mouse serum in cultures of mouse L929 cells. 1 μg/ml MP-3 induced an intensive production of interferon by human cells, both L41 and donor PBC. 0.01 μg/ml MP-4 showed induction of interferon synthesis comparable to MP-3 in L-41 cells. MP-5 at small doses (0.001 μg/ml induced interferon in donor PBC, and at larger doses (1 μg/ml) was active with L-41 cells. MP-6 induced relatively small amounts of interferon in both L-41 and donor PBC.

RIV-Inhibition by MPs In Vitro

The anti-viral activity of MP-3, MP-4, MP-5 and MP-6 was examined using in vitro culture of MT4 cells, a human T-lymphoblastoid cell line infected by HIV. As a source of infective virus, the laboratory HT HIV 27 virus strain was used. It was capable of causing chronic HIV-infection, with the production of non-damaged HIV-1 infective particles in MT4 cells in vitro.

The intensity. of HIV infection and the respective anti-HIV influence of the MPs was evaluated according to the following criteria:

(a) alterations of normal MT4 cell morphology induced by HIV (cytopathogenic effect);

(b) HIV antigens found in infected MT4 cells using luminescence microscopy of the cells pre-labelled with fluorescent anti-HIV antibodies;

(c) HIV proteins detected in HIV-infected MT4 cell culture medium using immunofluorescence.

The HIV-infected MT4 cells were incubated in RPMI-1640 culture medium supplemented with 10% FBS and 2 mM L-glutamine. The MT4 cells (0.5 million cells per 1 ml of culture medium) were placed in wells of a 24-well plastic culture plates and kept for 7 days of 37° C. in an atmosphere of 4.5% $CO_2$. Each of the MPs examined was added into respective wells of the culture plates, to final concentrations of 0.1, 0.5, 1, 5, 10, 50 and 100 μg per 1 ml of culture were used. Azidothymidine (Sigma Chemical Co.) at its final concentration of 0.1 μg/ml, was used as a positive anti-viral control during each of the experiments.

Standard cell viability tests performed 24 h from cultivation showed MP-3, MP-4, MP-5 and MP-6 caused no visible damage of MT4 cells growing in vitro. Of these four compounds, the most pronounced anti-HIV activity was observed with MP-3. In the presence of 1–5 μg/ml or higher concentration of MP-3, HIV replication was completely stopped: no cytopathogenic effect or production of viral protein was recorded in such cultures. 50 % inhibition of HIV replication was observed in the presence of 10 μg/ml MP-4. MP-5 and MP-6 did not influence on HIV replication in MT4 cell cultures in vitro. Azidothymidine (0.1 μg/ml) caused 100% inhibition of HIV replication in the infected MT-4 cells.

What is claimed is:

1. An isolated peptide selected from the group consisting of Lea-Val-Cys-Tyr-Pro-Gln (SEQ ID NO: 3), Phe-Arg-Pro-Arg-Ile-Met-Thr-Pro (SEQ ID NO: 4), and Val-Val-Tyr-Pro-Asp (SEQ ID NO: 5).

2. The peptide according to claim 1, wherein the peptide is Leu-Val-Cys-Tyr-Pro-Gln (SEQ ID NO: 3).

3. The peptide according to claim 1, wherein the peptide is Phe-Arg-Pro-Arg-Ile-Met-Thr-Pro (SEQ ID NO: 4).

4. The peptide according to claim 1, wherein the peptide is Val-Val-Tyr-Pro-Asp (SEQ ID NO: 5).

5. A composition comprising a peptide selected from the group consisting of Leu-Val-Cys-Tyr-Pro-Gln (SEQ ID NO: 3), Phe-Arg-Pro-Arg-Ile-Met-Thr-Pro (SEQ ID NO: 4), and Val-Val-Tyr-Pro-Asp (SEQ ID NO: 5) together with a carrier or diluent and an adjuvant.

6. The composition according to claim 5, wherein the peptide is Leu-Val-Cys-Tyr-Pro-Gln (SEQ ID NO: 3).

7. The composition according to claim 5, wherein the peptide is Phe-Arg-Pro-Arg-Ile-Met-Thr-Pro (SEQ ID NO: 4).

8. The composition according to claim 5, wherein the peptide is Val-Val-Tyr-Pro-Asp (SEQ ID NO: 5).

9. A method of inhibiting proliferation of bacteria comprising administering to a patient in need thereof a peptide selected from the group consisting of Leu-Val-Cys-Tyr-Pro-Gln (SEQ ID NO: 3), Phe-Arg-Pro-Arg-Ile-Met-Thr-Pro (SEQ ID NO: 4), and Val-Val-Tyr-Pro-Asp (SEQ ID NO: 5) for a time and under conditions effective to inhibit proliferation of said bacteria.

10. The method according to claim 9, wherein the peptide is Leu-Val-Cys-Tyr-Pro-Gln (SEQ ID NO: 3).

11. The method according to claim 9, wherein the peptide is Phe-Arg-Pro-Arg-Ile-Met-Thr-Pro (SEQ ID NO: 4).

12. The method according to claim 9, wherein the peptide is Val-Val-Tyr-Pro-Asp (SEQ ID NO: 5).

13. A method of inhibiting HIV replication comprising administering to a patient in need thereof a peptide selected from the group consisting of Leu-Val-Cys-Tyr-Pro-Gln (SEQ ID NO: 3), Phe-Arg-Pro-Arg-Ile-Met-Thr-Pro (SEQ ID NO: 4), and Val-Val-Tyr-Pro-Asp (SEQ ID NO: 5) for a time and under conditions effective to inhibit HIV replication.

14. The method according to claim 13, wherein the peptide is Leu-Val-Cys-Tyr-Pro-Gln (SEQ ID NO: 3).

15. The method according to claim 13, wherein the peptide is Phe-Arg-Pro-Arg-Ile-Met-Thr-Pro (SEQ ID NO: 4).

16. The method according to claim 13, wherein the peptide is Val-Val-Tyr-Pro-Asp (SEQ ID NO: 5).

* * * * *

UNITED STATES PATENT AND TRADEMARK OFFICE
CERTIFICATE OF CORRECTION

PATENT NO.    : 6,469,137 B1
DATED         : October 22, 2002
INVENTOR(S)   : Rem V. Petrov et al.

It is certified that error appears in the above-identified patent and that said Letters Patent is hereby corrected as shown below:

<u>Column 7,</u>
Line 35, "Lea-Val-Cys-Tyr-Pro-Gln" should read -- Leu-Val-Cys-Tyr-Pro-Gln --.

Signed and Sealed this

Eighteenth Day of February, 2003

JAMES E. ROGAN
*Director of the United States Patent and Trademark Office*